US00PP33402P2

(12) United States Plant Patent
Hartman

(10) Patent No.: US PP33,402 P2
(45) Date of Patent: Aug. 24, 2021

(54) ***CALADIUM* PLANT NAMED 'PCL 1522-50'**

(50) Latin Name: ***Caladium* x *hortulanum***
Varietal Denomination: PCL 1522-50

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/013,799

(22) Filed: Sep. 7, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. Anne Whealy

(57) ABSTRACT

A new and distinct cultivar of *Caladium* plant named 'PCL 1522-50', characterized by its intermediate height; somewhat mounding plant habit; dense and bushy appearance; vigorous growth habit and rapid growth rate; fancy-type leaves that are dark pink in color with light yellowish green-colored venation and dark green-colored margins; and petioles that are dark brownish green in color or green with darker-colored streaks, stippling and tessellations.

7 Drawing Sheets

Figure 1:
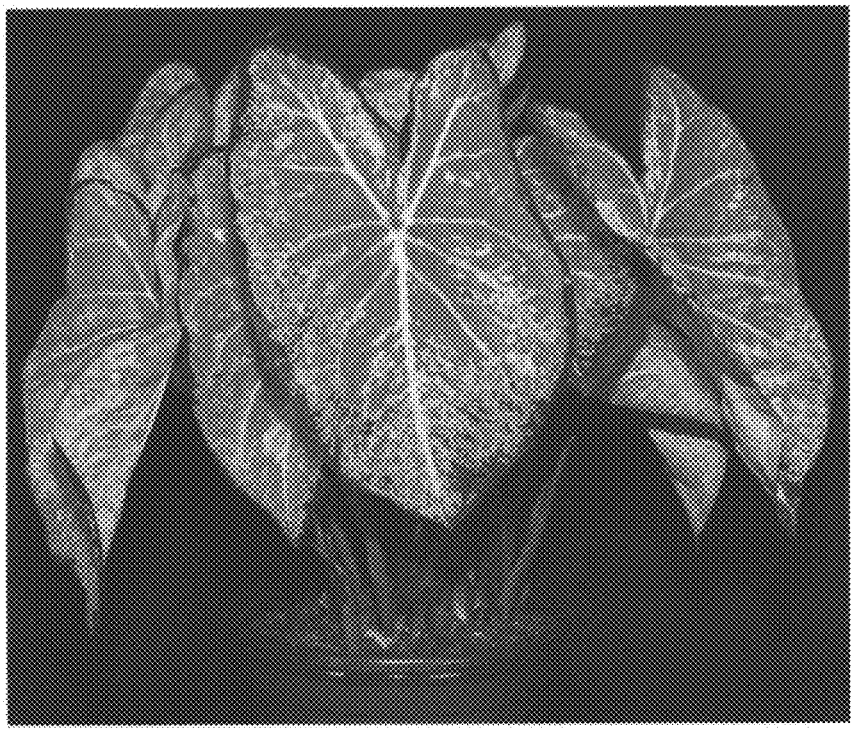

Botanical designation: *Caladium* x *hortulanum*.
Cultivar denomination: 'PCL 1522-50'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* x *hortulanum*, commercially referred to as a fancy leaf-type *Caladium* and hereinafter referred to by the name 'PCL 1522-50'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* x *hortulanum* 'White Wonder', disclosed in U.S. Plant Pat. No. 21,044, as the female, or seed, parent with *Caladium* x *hortulanum* 'Pink Beauty', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PCL 1522-50'. These characteristics in combination distinguish 'PCL 1522-50' as a new and distinct *Caladium* plant:

1. Intermediate in height and somewhat mounding plant habit; dense and bushy appearance.
2. Vigorous growth habit and rapid growth rate.
3. Fancy-type leaves that are dark pink in color with light yellowish green-colored venation and dark green-colored margins.
4. Petioles that are dark brownish green in color or green with darker-colored streaks, stippling and tessellations.

Plants of the new *Caladium* differ primarily from plants of the female parent, 'White Wonder', in the following characteristics:

1. Plants of the new *Caladium* are taller and more upright than plants of 'White Wonder'.
2. Plants of the new *Caladium* have fancy type leaves whereas plants of 'White Wonder' have lance type leaves.

3. Plants of the new *Caladium* and 'White Wonder' differ in leaf color as leaves of the new *Caladium* are dark pink in color with light yellowish green-colored venation and dark green-colored margins whereas leaves of 'White Wonder' are white to grey-green in color with light pink to white-colored venation and dark green-colored borders.

Plants of the new *Caladium* differ primarily from plants of the male parent, 'Pink Beauty', in the following characteristics:

1. Plants of the new *Caladium* are larger and have larger leaves than plants of 'Pink Beauty'.
2. Plants of the new *Caladium* grow slower than plants of 'Pink Beauty'.
3. Plants of the new *Caladium* and 'Pink Beauty' differ in leaf color as leaves of the new *Caladium* are dark pink in color with light yellowish green-colored venation and dark green-colored margins whereas leaves of 'Pink Beauty' are olive green in color with random pink-colored blotches and bright pink to reddish purple-colored venation.

Plants of the new *Caladium* can be compared to plants of *Caladium* x *hortulanum* 'Pink Cloud', not patented. In side-by-side comparisons, plants of the new *Caladium* differ primarily from plants of 'Pink Cloud' in the following characteristics:

1. Plants of the new *Caladium* and 'Pink Cloud' differ in leaf color as leaves of the new *Caladium* are dark pink in color with light yellowish green-colored venation and dark green-colored margins whereas leaves of plants of 'Pink Cloud' are pale pink in color with narrow green-colored margins and venation that is creamy white flushed with pink in color.
2. Plants of the new *Caladium* and 'Pink Cloud' in leaf petiole color as leaf petioles of the new *Caladium* are dark brownish green in color or green with darker-colored streaks, stippling and tessellations whereas leaf petioles of 'Pink Cloud' are pale greenish with brownish green-colored streaks, stippling and tessellations.

Plants of the new *Caladium* also can be compared to plants of *Caladium* x *hortulanum* 'Pink Splash', disclosed in U.S. Plant Pat. No. 23,792. In side-by-side comparisons, plants of the new *Caladium* differ primarily from plants of 'Pink Splash' in the following characteristics:

1. Plants of the new *Caladium* and 'Pink Splash' differ in leaf color as leaves of the new *Caladium* are dark pink in color with light yellowish green-colored venation and dark green-colored margins whereas leaves of plants of 'Pink Splash' have dark green-colored venation, red purple-colored interveinal areas and dark green-colored margins.
2. Plants of the new *Caladium* and 'Pink Splash' in leaf petiole color as leaf petioles of the new *Caladium* are dark brownish green in color or green with darker-colored streaks, stippling and tessellations whereas leaf petioles of 'Pink Splash' are tannish pink in color with darker-colored streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'PCL 1522-50' in a container and grown in a shade house (tuber de-eyed).

Figure 2:
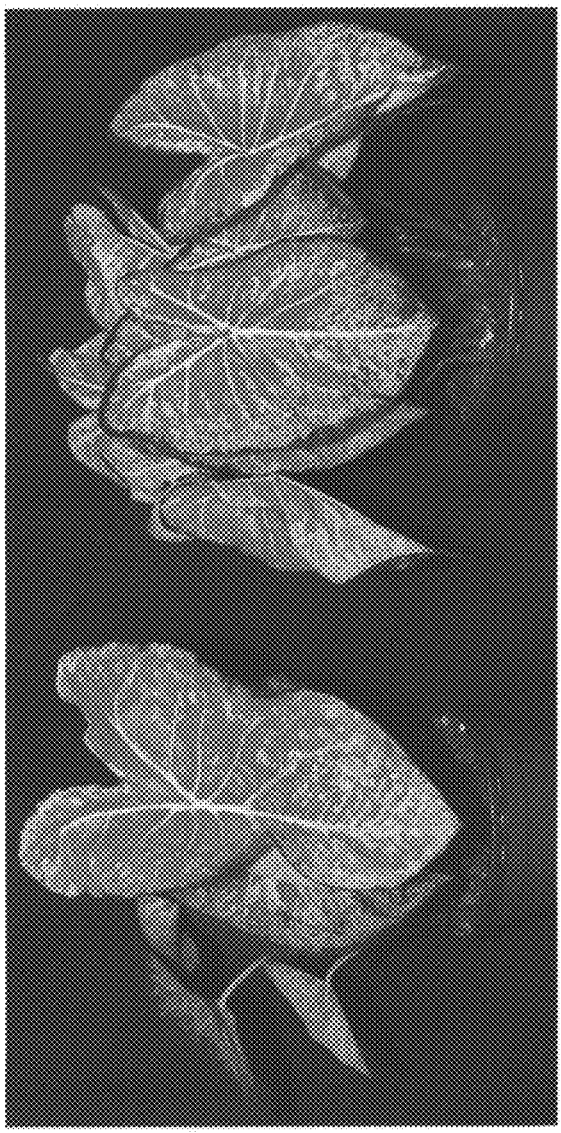
Figure 3:
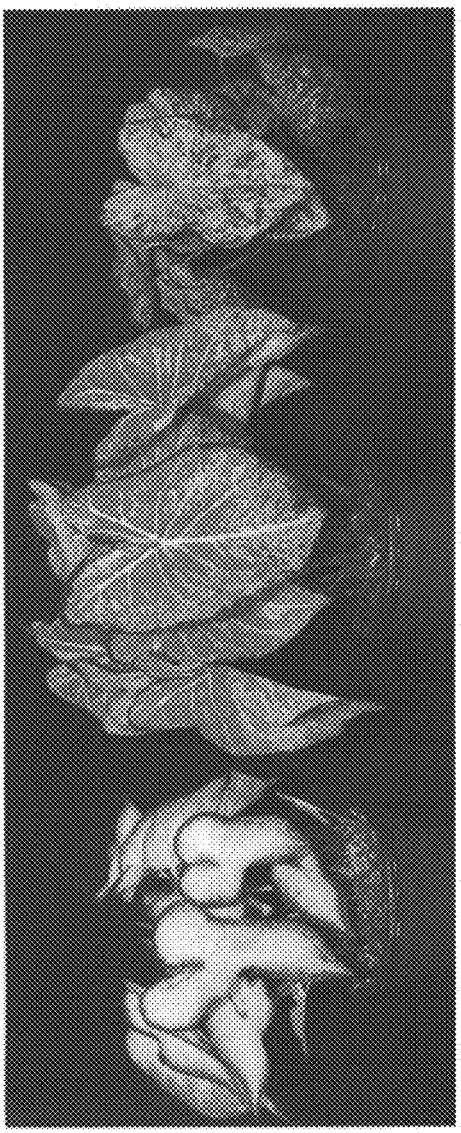

The photograph on the second sheet (FIG. 2) is a comparison view of typical plants of 'PCL 1522-50' grown in containers, the plant on the left has not had its tuber de-eyed and the plant on the right has had its tuber de-eyed prior to planting; the photograph on the third sheet (FIG. 3) is side perspective view of the female parent, 'White Wonder' (left), 'PCL 1522-50' (center) and the male parent, 'Pink Beauty' (right).

Figure 4:
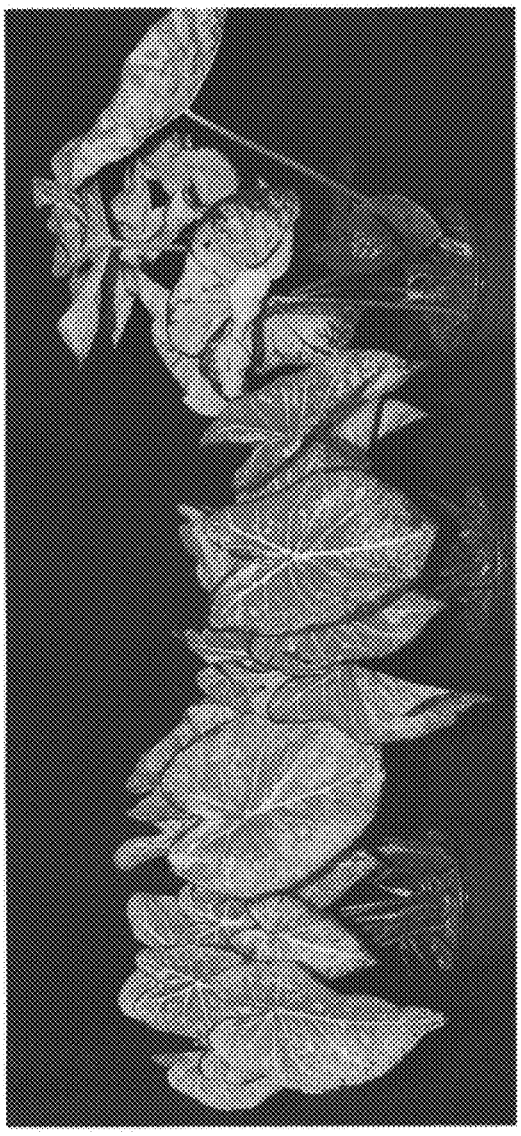

The photograph on the fourth sheet (FIG. 4) is a comparison view of typical potted plants of 'Pink Cloud' (left), 'PCL 1522-50' (center) and 'Pink Splash' (right).

Figure 5:
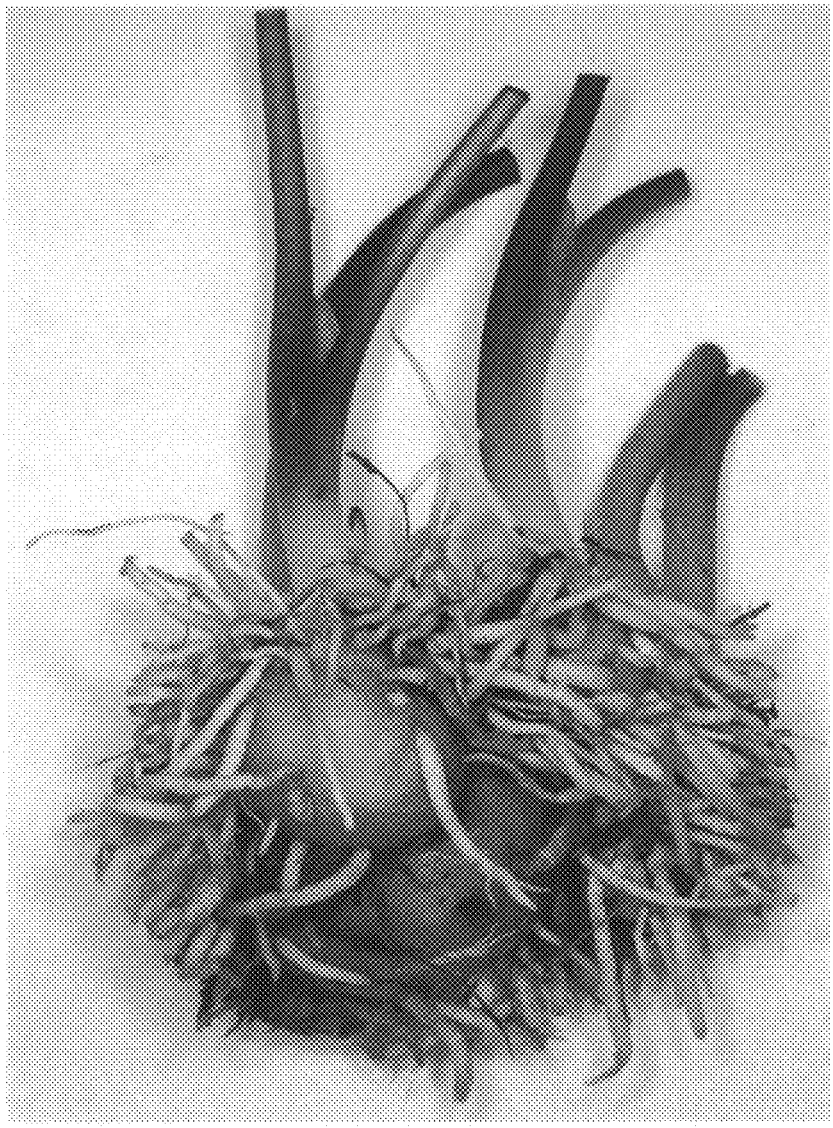

The photograph on the fifth sheet (FIG. 5) is a close-up view of typical freshly-harvested tubers with roots and leaf petioles of 'PCL 1522-50'.

Figure 6:
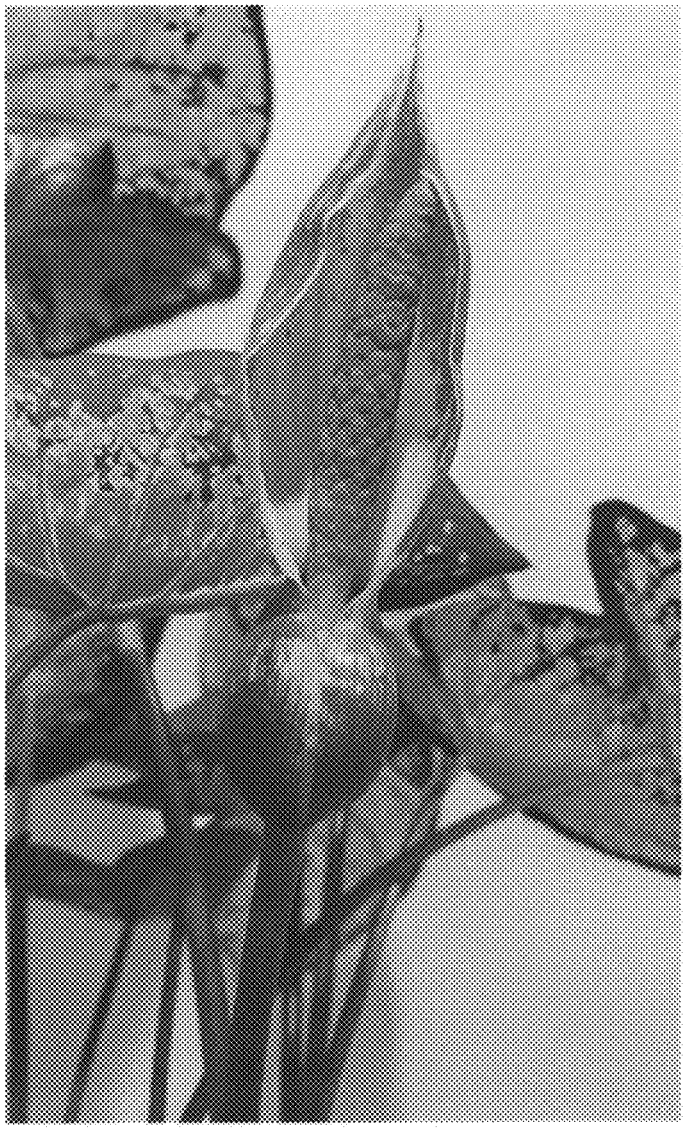

The photograph on the sixth sheet (FIG. 6) is a close-up view of a typical inflorescence of 'PCL 1522-50'.

Figure 7:
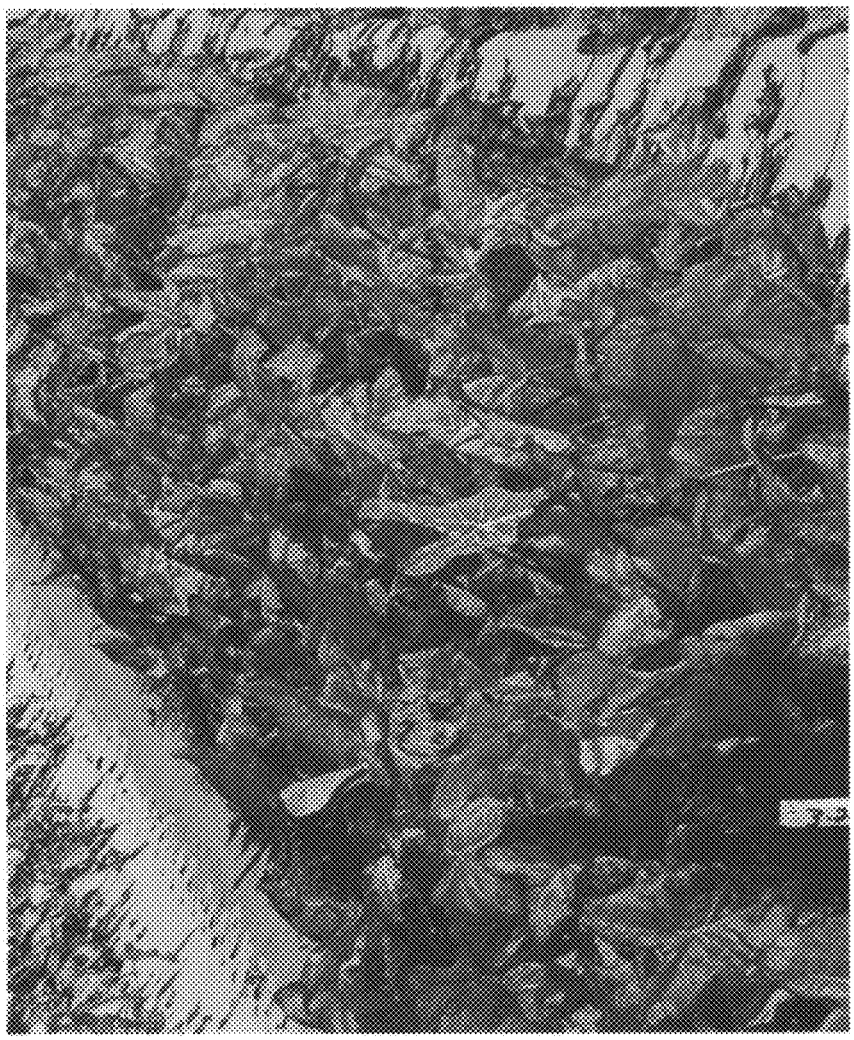

The photograph on the seventh sheet (FIG. 7) is a side perspective view of typical plants of 'PCL 1522-50' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33 ° C., night temperatures ranged from about 22 ° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were eight weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Caladium* x *hortulanum* 'PCL 1522-50'.

Parentage:

*Female, or seed, parent.*—*Caladium* x *hortulanum* 'White Wonder' disclosed in U.S. Plant Pat. No. 21,044.

*Male, or pollen, parent.*—*Caladium* x *hortulanum* 'Pink Beauty', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments mostly elliptic to ovate in shape. Height: About 3.7 cm. Diameter: About 8.5 cm to 9.8 cm. Segment height: About 2.3 cm to 3.2 cm. Segment diameter: About 2.2 cm to 3.2 cm. Axillary bud shape: Roughly triangular. Axillary bud size: About 4 mm by 5 mm. Texture: Thick, starchy; somewhat brittle. Color: Periderm, freshly-harvested: Close to 199B. Periderm, dried: Close to 200D. Epidermis: Close to 158D. Cortical tissue: Close to 2D. Axillary buds: Close to 36C and 36D. Root description: Thick, fleshy contractile roots with few lateral branches; color, close to 155C tinged with close to 37D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height, upright and somewhat mounding plant habit; dense and bushy appearance; vigorous growth habit and rapid growth rate; potted plants finish in saleable form in about five to seven weeks after planting tubers; leaf petioles and leaves arise from one or more growing points on tubers; leaf petioles initially upright and leaning and arching outwardly with development.

*Plant height, from soil level to top of foliar plane, shade house-grown potted plants*.—About 25.5 cm to 31 cm.

*Plant height, from soil level to top of floral plane, shade house-grown potted plants*.—About 33.5 cm.

*Plant diameter or spread, shade house-grown potted plants*.—About 36 cm to 43 cm.

*Number of shoots per plant, shade house-grown potted plants, tubers de-eyed*.—About five to seven develop per #1 tuber.

*Number of shoots per plant, shade house-grown potted plants, tubers not de-eyed*.—About three to four develop per #1 tuber.

*Cataphylls, shade house-grown potted plants*.—Length: About 6.5 cm to 8.8 cm. Width: About 1 cm to 1.8 cm. Shape: Lanceolate. Apex: Acute to emarginate. Base: Sheathing the stem. Color: Outer surface: Close to N199A and 200A; color becoming closer to N199B faintly tinged with close to 187A with development. Inner surface: Close to 200D tinged with close to 185D; colors and patterns on outer surface visible on inner surface.

Leaf description:

*Arrangement and type*.—Alternate; simple; fancy-type.

*Length, shade house-grown potted plants*.—About 19.5 cm to 27 cm.

*Width, shade house-grown potted plants*.—About 12.8 cm to 15 cm; when flattened, about 13 cm to 15.5 cm.

*Shape*.—Ovate to cordate.

*Apex*.—Acute.

*Base*.—Sagittate-peltate, cordate.

*Margin*.—Entire; mostly flat with broad undulations.

*Texture and luster, upper surface*.—Rugose, glabrous; leathery; dull sheen.

*Texture and luster, lower surface*.—Rugose, glabrous; veins are glaucous; dull sheen.

*Venation pattern*.—Pinnate and palmate.

*Color, shade house-grown potted plants*.—Fully developed leaves, upper surface: Background color: Close to 51A and 51B; random white spots, close to 155B. Margins: Close to 147A. Basal notch: Close to 187C and 53A. Midvein: Distally, close to 145C and 145D with flecks and streaks, close to 147A and 147B; proximally, close to 157A and 157B with flecks, close to 147B and occasionally tinged with close to 182B and 182C. Primary and secondary venation: Close to 157B with flecks, close to 147B. Fully developed leaves, lower surface: Background color: Close to 49C, 49D, 51D, 59C and 59D; random sectors, close to 145C with flecks, close to 146B. Margins: Close to 191A tinged with close to 189A. Leaf attachment point: Close to 187B and 187C. Midvein: Close to 145C and 145D; areas surrounding midvein, close to 158D and 155C. Primary and secondary venation: Close to 146B and 146C; areas surrounding midvein, close to 158D and 155C.

*Petioles*.—Aspect: Initially upright and straight and leaning and arching outwardly with development; flexible. Length, shade house-grown potted plants: About 22 cm to 25.5 cm. Diameter, distally, shade house-grown potted plants: About 4 mm to 5 mm. Diameter, proximally, shade house-grown potted plants: About 7 mm to 8 mm. Texture and luster: Smooth, glabrous; glaucous; dull sheen. Color, shade house-grown potted plants: Fully developed: Close to 147B flushed with close to N199A or close to 147C tinged with close to 199D and stippled, streaked and tessellated with close to 147A to 147B tinged with close to N199A; just below the leaf junction, close to N170D and 49D flushed with close to 199A and stippled, streaked and tessellated with close to 199A. Wing length, shade house-grown potted plants: About 6 cm to 7.2 cm. Wing diameter, shade house-grown potted plants: About 8 mm to 10 mm. Texture and luster, inner and outer surfaces: Smooth, glabrous; glossy. Wing color, shade house-grown potted plants: Outer surface: Close to N170D and 49D with dense streaks and stippling of close to 147A; apex and distal margins flushed with close to 49C. Inner surface: Close to N158D; colors and patterns on the outer surface are visible on the inner surface.

Inflorescence description: Inflorescences observed on nine week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint note.

*Natural flowering season and flower longevity*.—Plants of the new *Caladium* typically flower during the spring and summer in central Florida; flowers develop about nine to ten weeks after growth commences; inflorescences last about three days before fading; inflorescences persistent.

*Spathe*.—Length, overall: About 10 cm. Length, distal open portion: About 7.5 cm. Length, proximal closed portion: About 2.5 cm. Width, distal open portion: About 2.5 cm. Depth, distal open portion: About 2.5 cm. Width, at constriction: About 1 cm to 1.6 cm. Width, proximal closed portion: About 2.2 cm. Shape, open portion: Ovate, elliptic. Apex: Acute. Base: Acute. Margin: Entire. Texture and luster, front surface: Smooth, glabrous; dull sheen. Texture and luster, rear surface: Smooth, glabrous; dull sheen and proximally, glaucous. Color, front surface: Distal open portion: Close to 155C and distally, mottled and flushed with close to 53C; with development, color becoming closer to N199B tinged with close to 187B and 187C. Proximal closed portion: Close to 147D and towards the base, faintly and sparsely flushed with close to N186C; color does not change with development. Color, rear surface: Distal open portion: Close to 155C; proximally and venation, close to 145C and 145D and distally, mottled and flushed with close to 53D; color does not change with development. Proximal closed portion: Close to 147B, 147C and 147D mottled and flecked with close to 148C and 148D; color does not change with development.

*Spadix*.—Length, overall: About 7.7 cm. Length, male flower zone: About 5 cm. Length, sterile zone: About 1.3 cm. Length, female flower zone: About 1.4 cm. Diameter, male flower zone: About 8 mm. Diameter, sterile flower zone: About 5 mm. Diameter, female flower zone: About 9 mm. Shape: Columnar, spindle-shaped. Apex: Acute. Base: Obtuse. Aspect: Upright. Color, mature, male zone: Close to 145B and 145C. Color, mature, sterile zone: Close to 158D. Color, mature, female zone: Close to 155D and 157D. Male flowers: Quantity per spadix: About 180. Shape: Obovate. Height: About 3.2 mm to 3.5 mm. Diameter: About 2.5 mm to 3 mm. Pollen amount: Moderate. Pollen color: Close to 11D. Female flowers: Quantity per spadix: About 168. Shape: Obovate. Height: About 2 mm. Diameter: About 1.2 mm. Stigma color: Close to 155D. Ovary color: Close to 157D.

*Scape*.—Length: About 23.5 cm. Diameter: About 4.5 mm. Strength: Sturdy; flexible. Aspect: Mostly erect. Texture and luster: Smooth, glabrous; dull to slightly glossy. Color: Close to 147C tinged with close to 199D and stippled, streaked and tessellated with close to 147A to 147B tinged with close to N199A; just below spathe, glaucous and close to 147B to 147C tinged with close to 146B to 146C and faintly stippled and streaked with close to N199A.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'PCL 1522-50' as illustrated and described.

* * * * *